United States Patent
Andreas et al.

(10) Patent No.: US 7,241,308 B2
(45) Date of Patent: Jul. 10, 2007

(54) STENT DEPLOYMENT SYSTEMS AND METHODS

(75) Inventors: Bernard Andreas, Redwood City, CA (US); David W. Snow, Menlo Park, CA (US); Jeffry J. Grainger, Portola Valley, CA (US)

(73) Assignee: Xtent, Inc., Menlo Park, CA (US)

( * ) Notice: Subject to any disclaimer, the term of this patent is extended or adjusted under 35 U.S.C. 154(b) by 249 days.

(21) Appl. No.: 10/458,062

(22) Filed: Jun. 9, 2003

(65) Prior Publication Data

US 2004/0249435 A1    Dec. 9, 2004

(51) Int. Cl.
*A61F 2/06* (2006.01)
(52) U.S. Cl. .................................... 623/1.11
(58) Field of Classification Search ........ 606/191–198; 623/1.11, 1.12, 1.15; 604/101.01, 101.02, 604/1.16
See application file for complete search history.

(56) References Cited

U.S. PATENT DOCUMENTS

| | | | |
|---|---|---|---|
| 4,564,014 A | 1/1986 | Fogarty et al. | |
| 4,733,665 A | 3/1988 | Palmaz | |
| 4,739,762 A | 4/1988 | Palmaz | |
| 4,776,337 A | 10/1988 | Palmaz | |
| 4,886,062 A | 12/1989 | Wiktor | |
| 4,994,066 A | 2/1991 | Voss | |
| 4,994,069 A | 2/1991 | Ritchart et al. | |
| 5,092,877 A | 3/1992 | Pinchuk | |
| 5,102,417 A | 4/1992 | Palmaz | |
| 5,195,984 A | 3/1993 | Schatz | |
| 5,226,913 A | 7/1993 | Pinchuk | |
| 5,246,421 A | 9/1993 | Saab | |
| 5,273,536 A | 12/1993 | Savas | |
| 5,421,955 A | 6/1995 | Lau et al. | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,554,181 A * | 9/1996 | Das ........................... | 623/1.12 |
| 5,571,086 A | 11/1996 | Kaplan et al. | |
| 5,607,463 A | 3/1997 | Schwartz et al. | |
| 5,628,775 A | 5/1997 | Jackson et al. | |
| 5,634,928 A | 6/1997 | Fischell et al. | |
| 5,676,654 A | 10/1997 | Ellis et al. | |
| 5,697,948 A | 12/1997 | Marin et al. | |
| 5,723,003 A * | 3/1998 | Winston et al. ............ | 623/1.13 |

(Continued)

FOREIGN PATENT DOCUMENTS

WO    WO 00/15151 A1    3/2000

(Continued)

*Primary Examiner*—Kevin T. Truong
(74) *Attorney, Agent, or Firm*—Townsend and Townsend and Crew LLP; Jeffry Grainger, Esq.

(57) ABSTRACT

A stent deployment system includes a catheter shaft, an expandable member mounted to the catheter shaft, and one or more stents or stent segments slidably positioned on the expandable member. The stent deployment system is adapted for deployment of stents or stent segments in very long lesions and in tapered and curved vessels. The stent deployment system facilitates slidable movement of a stent in a distal direction relative to the expandable member while inhibiting slidable movement in a proximal direction relative to the expandable member.

28 Claims, 9 Drawing Sheets

U.S. PATENT DOCUMENTS

| | | | |
|---|---|---|---|
| 5,735,869 A | 4/1998 | Fernandez-Aceytuno |
| 5,749,848 A | 5/1998 | Jang et al. |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,807,398 A | 9/1998 | Shaknovich |
| 5,833,694 A | 11/1998 | Poncet |
| 5,843,092 A | 12/1998 | Heller et al. |
| 5,858,556 A | 1/1999 | Eckert et al. |
| 5,891,190 A | 4/1999 | Boneau |
| 5,895,398 A | 4/1999 | Wensel et al. |
| 5,902,332 A | 5/1999 | Schatz |
| 5,961,536 A | 10/1999 | Mickley et al. |
| 5,976,155 A | 11/1999 | Foreman et al. |
| 5,980,552 A | 11/1999 | Pinchasik |
| 6,022,359 A | 2/2000 | Frantzen |
| 6,090,063 A | 7/2000 | Makower et al. |
| 6,090,136 A | 7/2000 | McDonald et al. |
| 6,143,016 A | 11/2000 | Bleam et al. |
| 6,187,034 B1 | 2/2001 | Frantzen |
| 6,190,402 B1 | 2/2001 | Horton et al. |
| 6,241,691 B1 | 6/2001 | Ferrera et al. |
| 6,251,134 B1 | 6/2001 | Alt et al. |
| 6,254,628 B1 | 7/2001 | Wallace et al. |
| 6,258,117 B1 | 7/2001 | Camrud et al. |
| 6,315,794 B1 | 11/2001 | Richter |
| 6,357,104 B1 | 3/2002 | Myers |
| 6,419,693 B1 | 4/2002 | Fariabi |
| 6,383,171 B1 | 5/2002 | Gifford et al. |
| 6,451,025 B1 | 9/2002 | Jervis |
| 6,451,050 B1 | 9/2002 | Rudakov et al. |
| 6,468,299 B2 | 10/2002 | Stack et al. |
| 6,485,510 B1 | 11/2002 | Camrud et al. |
| 6,511,468 B1 | 1/2003 | Cragg et al. |
| 6,520,987 B1 | 2/2003 | Plante |
| 2002/0138132 A1 | 9/2002 | Brown |
| 2002/0156496 A1 | 10/2002 | Charmoni |

FOREIGN PATENT DOCUMENTS

| | | |
|---|---|---|
| WO | WO 00/32136 A1 | 6/2000 |
| WO | WO 03/022178 A1 | 3/2003 |

* cited by examiner

STENT DEPLOYMENT SYSTEMS AND METHODS

BACKGROUND OF THE INVENTION

In coronary artery disease, stenotic plaques form within the coronary arteries, restricting and in some cases completely blocking blood flow to the heart muscle. In recent years, a number of different catheter-based interventions have been developed to treat coronary artery disease, including percutaneous transluminal coronary angioplasty (PTCA) and stenting. PTCA involves the placement of an endovascular catheter into the diseased coronary artery and expanding a balloon within the stenotic lesion to dilate the lumen, thereby improving blood flow through the treated area. One drawback of PTCA has been the tendency in some cases for the coronary artery lumen to "restenose" following dilatation, wherein plaque reforms at the treatment site to narrow or block the lumen. Coronary stenting has been developed in part to address this restenosis problem. In coronary stenting, a tubular stent is positioned within the coronary lesion using an endovascular delivery catheter. The stent is expanded within the lesion and implanted in its expanded state, maintaining the patency of the arterial lumen.

Even after stenting, however, some patients experience restenosis. While the causes of restenosis are not fully understood, a number of different technologies have been developed to reduce restenosis following stenting. One such technology that has shown a great deal of promise is the use of drug-coated stents that gradually elute anti-stenosis agents into the wall of the coronary artery. Another approach is the use of radioactive stents that deter cell proliferation at the treatment site. A further approach involves the optimization stent geometry and maximizing stent flexibility to reduce the vascular response that results in cell proliferation following stent placement.

With these new stent technologies showing promising reductions in restenosis rates, stents may begin to be used in new and different ways. Stents may be used in arteries of shape and size heretofore untreatable, both in the coronary vasculature and in other parts of the body. Stents of substantially greater length may be used to treat longer lesions than has been possible before. Stents may be used to "pave" long sections of diseased or disease-prone arteries. Stents may be deployed in arteries that are much smaller than could be stented before, in highly curved vessels, as well as in more tapered vessels.

Current stents and stent deployment devices, however, are not well-suited to address these new potential applications for stents. For example, current stents are designed for treating relatively short lesions, and often are not suitable for longer lesions through which the vessel may be curved, tapered or have other complex geometries. Likewise, current stent deployment catheters function effectively to deliver stents of relatively short length in shorter vascular lesions, but they do not perform well in treating longer, tapered, and/or curved vessels. For example in tapered vessels, current stent deployment catheters may fail to fully expand the stent at its proximal end, while potentially over-expanding the stent at its distal end. Moreover, current stent and stent delivery technology is limited to deploying stents of predetermined length, requiring advance selection of a stent and associated catheter to match the lesion to be treated. Following introduction of the device, should the user wish to treat a longer section of the vessel, the user must remove the delivery catheter from the body and exchange it for a different catheter having a longer stent, or attempt to deploy multiple stents in close proximity to one another, each requiring introduction of new delivery catheter.

What is needed, therefore, is a stent delivery catheter suitable for deployment of long or short stents in long or short vascular lesions and in curved or tapered vessels. The stent delivery catheter should be further adapted for delivering multiple independent, stents or stent segments simultaneously or serially, as well as for selecting and deploying a stent of desired length without removing the delivery catheter from the body.

BRIEF SUMMARY OF THE INVENTION

The present invention provides stent delivery catheters, systems and methods for deploying stents in body lumens. While the invention will have application in a number of different vessels in various parts of the body, the invention is particularly well-suited for stenting of the coronary arteries, saphenous veins and other grafts, and peripheral arteries including the carotid and femoral arteries. The invention is particularly advantageous in its ability to deploy stents in relatively long vascular lesions that have tapers, curves, or other complex geometries. Moreover, in a preferred embodiment, the invention enables the user to select and deploy one or more stents of desired length in situ without removing or exchanging catheters.

In a first aspect, the invention provides a stent deployment system for deploying one or more stents in a vessel, the stent deployment system including an elongated catheter with an expandable member near its distal end. The expandable member has proximal and distal extremities with different expanded diameters. In one embodiment, suited for use in tapered vessels, the proximal extremity has an expanded diameter larger than the expanded diameter of the distal extremity. A plurality of independent stent segments is slidably positionable on the proximal and distal extremities for expansion therewith, each stent segment being independently expandable to an expanded diameter potentially different than at least one other stent segment. The expandable member has an outer surface suitable for slidable advancement of the stent segments thereon from the proximal extremity to the distal extremity.

In various embodiments, proximal and distal extremities may be tapered, stepped, non-tapered (constant diameter), or combinations thereof. The proximal and distal extremities may be contiguous with one another, or may be separated by a portion of the expandable member. Between the proximal and distal extremities, the expandable member may be non-tapered, tapered at a constant or variable slope, or it may include two or more cylindrical steps of decreasing diameter. Alternatively, the expandable member may include a combination of tapered sections and stepped sections, or tapered sections and non-tapered sections. The outer surface of the expandable member is preferably configured to allow the stent segments to be slidably advanced toward the distal end of the expandable member (or the expandable member slidably retracted proximally relative to the stent segments) when the expandable member is in an unexpanded condition. This enables the user to position the desired number of stent segments to be deployed over the expandable member, thereby facilitating in situ customization of stent length. Further, following deployment of a stent or series of stent segments, an additional stent or series of segments may then be slidably positioned on the expandable member for subsequent deployment.

In an exemplary embodiment, either or both of the first and second extremities of the expandable member have an axial length selected to accommodate a pre-selected number of stent segments. For example, in stepped embodiments, each cylindrical step of the expandable member may be configured to accommodate one stent segment. Alternatively, the expandable member may have a non-tapered or less tapered distal extremity accommodating a specific number of stent segments, e.g five to ten, and a more tapered proximal extremity on which one or more stent segments may be positioned.

In a further aspect, the expandable member has a proximal end portion fixed to the catheter shaft at a first location and a distal end portion fixed to the catheter shaft at a second location. The proximal end portion has a reverse taper between the first location and the proximal extremity, and the distal end portion has a distal taper between the distal extremity and the second location. In a preferred embodiment, the expandable member is tapered between the proximal end portion and the distal end portion at a slope substantially less than the slope of the distal taper. Preferably, the outer surface is tapered at a slope of about 0.5% to 5%.

In another aspect of the invention, the stent deployment system includes a pusher for slidably advancing the stent segments distally relative to the expandable member. In a preferred embodiment, the pusher comprises a tubular member slidably disposed over the catheter shaft and having a distal end for engaging a stent segment. The pusher can be pushed distally relative to the expandable member to advance the stent segments thereon, or the expandable member may be pulled proximally relative to the stent segments while maintaining a distally directed force on the pusher so that the expandable member is positioned within the stent segments to be deployed.

In a preferred aspect of the invention, the expandable member is adapted to expand a first plurality of stent segments simultaneously while a second plurality of stent segments remains unexpanded. To accomplish this, the stent deployment system preferably includes a sheath slidably disposed over at least a proximal portion of the expandable member on which the second plurality of stent segments is disposed. The sheath is configured to restrain expansion of the proximal portion of the expandable member and the second plurality of stent segments when the distal portion of the expandable member is expanded. The sheath will have sufficient radial strength to resist expansion by the balloon as it is inflated. Preferably, the sheath has a metal braid or other reinforcement embedded in its wall.

In a further aspect, the invention provides a method of deploying stent segments in a blood vessel having a luminal taper. In a preferred embodiment, the method comprises transluminally introducing a catheter into the blood vessel, the catheter having an expandable member near a distal end thereof; positioning a first plurality of independent stent segments over the expandable member such that a first stent segment is on a proximal extremity of the expandable member and a second stent segment is on a distal extremity of the expandable member, the first and second stent segments being independently movable relative to the expandable member; and expanding the expandable member such that the proximal extremity has a first expanded diameter and the distal extremity has a second expanded diameter smaller than the first expanded diameter, wherein the first stent segment is expanded to a diameter larger than the second stent segment. According to the method of the invention, three, four, or more stent segments may be expanded simultaneously to the same or different diameters.

In still another aspect, the method includes a step of constraining a proximal portion of the expandable member from expansion while a distal portion of the expandable member is expanded, the proximal and distal extremities being in the distal portion. Usually, at least a third stent segment, and preferably a plurality of stent segments, is slidably disposed on the proximal portion. In a preferred embodiment, the expandable member is constrained by a sheath slidably disposed over the proximal portion of the expandable member along with the stent segments positioned thereon.

In a further embodiment, the method includes slidably positioning a second plurality of independent stent segments over the expandable member with the catheter remaining in the blood vessel. Preferably, the second plurality of independent stent segments is slidably positioned over the expandable member by a pusher slidably coupled to the catheter. In a preferred method, the second plurality of independent stent segments is slidably positioned over the expandable member by retracting the expandable member relative to the second plurality of independent stent segments while exerting a distal force on the pusher to maintain the stent segments in position. Either the first plurality of stent segments or the second plurality of stent segments, or both, may be slidably positioned over the expandable member while the catheter remains disposed in the blood vessel.

In a further aspect of the invention, a stent deployment system comprises an elongated catheter shaft having a proximal end and a distal end an expandable member mounted to the catheter shaft near the distal end, the expandable member having an outer surface; and a stent slidably positionable over the outer surface of the expandable member, wherein the outer surface is configured to allow sliding movement of the stent distally relative to the expandable member and inhibit sliding movement of the stent proximally relative to the expandable member.

In a preferred embodiment, the outer surface of the expandable member comprises a plurality of projections projecting outwardly therefrom. The projections point generally in a distal direction to facilitate movement of the stent distally relative thereto and to inhibit movement of the stent proximally relative thereto. In response to sufficient force the projections are resiliently deflectable so as to point generally in a proximal direction to allow movement of the stent proximally relative thereto. Preferably, the projections project at an angle from the outer surface, the angle being variable in response to tension in the outer surface. The angle of the projections may be varied either by exerting tension on the expandable member, or by partially inflating the expandable member.

In an alternative embodiment, the outer surface comprises a plurality of ribs configured to engage the stent. The ribs are preferably convex on a proximal side thereof to facilitate distal movement of the stent, while having a distal side configured to inhibit proximal movement of the stent. The ribs are deflectable in response to sufficient force to allow movement of the stent proximally relative thereto.

Further aspects of the nature and advantages of the invention will become apparent from the following detailed description when taken in conjunction with the drawings.

DETAILED DESCRIPTION OF THE INVENTION

Figure 1:
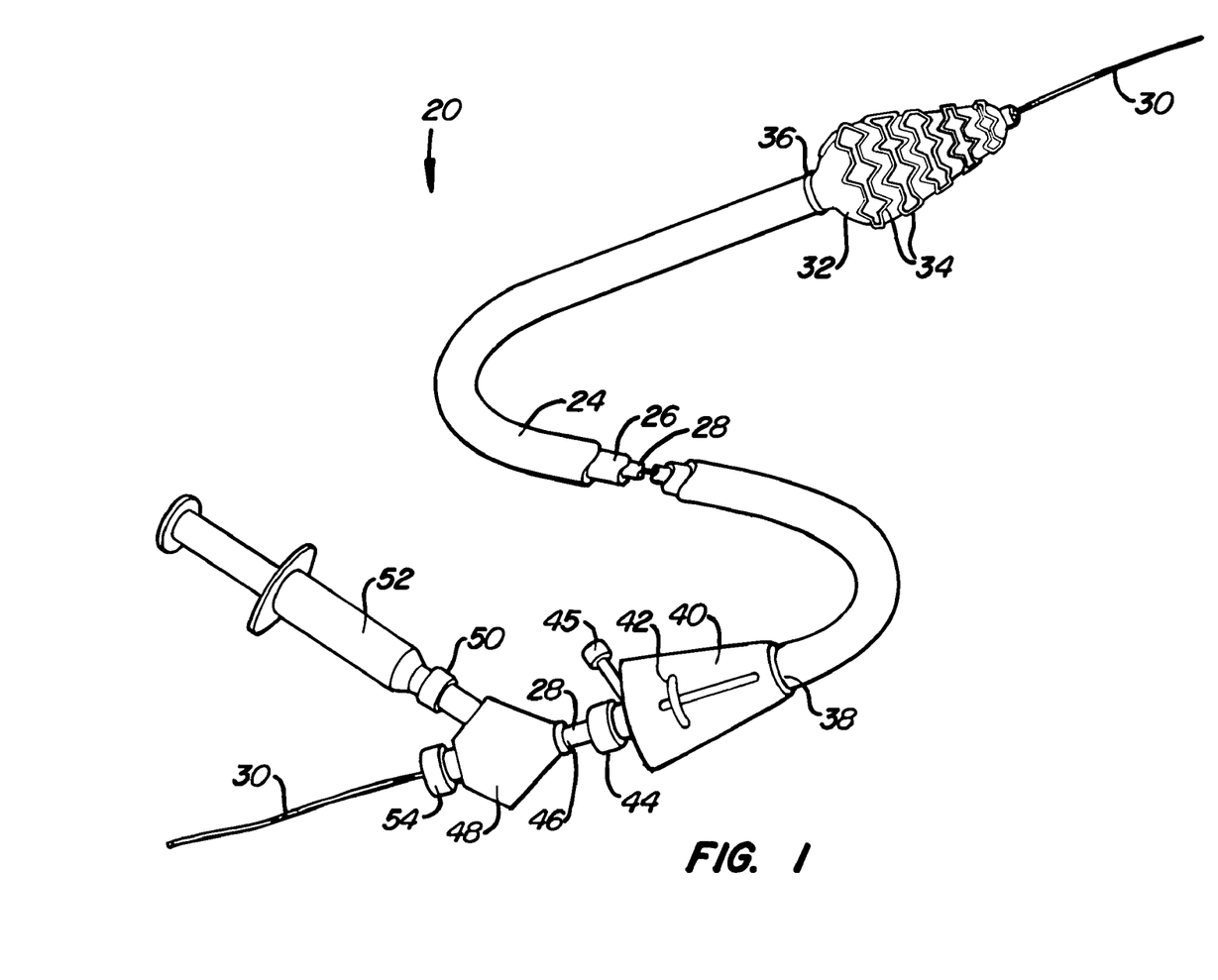
FIG. 1 is a perspective view of a stent deployment system according to the invention.

A preferred embodiment of a stent deployment system according to the invention is illustrated in FIG. 1. Stent deployment system 20 includes a sheath 24, a pusher tube 26 slidably disposed within sheath 24, and a catheter shaft 28 slidably disposed within pusher tube 26. Sheath 24, pusher tube 26 and catheter shaft 28 are all made of a flexible biocompatible material suitable for endovascular placement and positioning along a tortuous path from a peripheral vessel to the coronary arteries. A guidewire 30 is slidably positionable within catheter shaft 28 to facilitate introduction and tracking. An expandable member 32, which preferably is an elastomeric balloon, is mounted to the distal end of catheter shaft 28 and has an unexpanded shape suitable for endovascular positioning, and an expanded shape for deploying a stent within a vascular lumen. A series of tubular stent segments 34 are disposed about the periphery of expandable member 32 and are configured to be expanded by the expandable member into contact with the vessel wall.

Expandable member 32 has an expanded shape that is optimal for the size and geometry of the vascular region being treated. In a preferred embodiment, expandable member 32 has a tapered or partially tapered shape, wherein a proximal extremity of expandable member 32 had a larger diameter than a distal extremity thereof. This enables optimal expansion of stent segments 34 in tapered vessels, wherein one or more stent segments 34 in a proximal portion of the treated region should be expanded more than the stent segments 34 located more distally. Of course, expandable member 32 may have a variety of shapes suited to the region being treated, which are described below.

Stent segments 34 are preferably unconnected to each other, independently positionable relative to expandable member 32, independently expandable to various diameters, and provided with a geometry that optimizes vessel wall coverage and maximizes flexibility. This allows a selected number of stent segments 34 to be deployed to treat very long or very short lesions and in vascular regions that are highly curved or tapered. Stents and stent segments suitable for use with the present invention are disclosed in commonly-assigned, co-pending application Ser. No. 10/306,813, filed Nov. 27, 2002, and Provisional Application Ser. No. 60/440,839, filed Jan. 17, 2003, which are hereby incorporated by reference.

Sheath 24 has a distal end 36 that engages and constrains expansion of a proximal portion of expandable member 32 as will be described more fully below. Preferably, sheath 24 is reinforced to resist expansion when expandable member 32 is expanded, having a metal or polymeric braid or other type of reinforcement embedded in or disposed around the wall thereof. A proximal end 38 of sheath 24 is mounted to a handle 40. An actuator 42 is slidably mounted to handle 40 and is coupled to a proximal end of pusher tube 26. In this way, sliding actuator 42 along handle 40 causes pusher tube 26 to move relative to sheath 24. A sealed port 44 is mounted to the proximal end of handle 40 and is configured to receive catheter shaft 28 and provide a fluid-tight seal around it while allowing it to slide relative to handle 40. A flushport 45 mounted to sealed port 44 communicates with the interior of sheath 24 to allow for introduction of fluid for flushing and lubrication purposes.

Catheter shaft 28 has a proximal end 46 to which is mounted an adaptor 48. Adaptor 48 has a port 50 configured for coupling to an inflation device such as a syringe 52, which is used to deliver an inflation fluid to expandable member 32, as described below. Adaptor 48 further includes a hemostasis valve 54 adapted to receive guidewire 30 and provide a fluid-tight seal around it while still allowing it to slide relative to adaptor 48.

Figure 2:
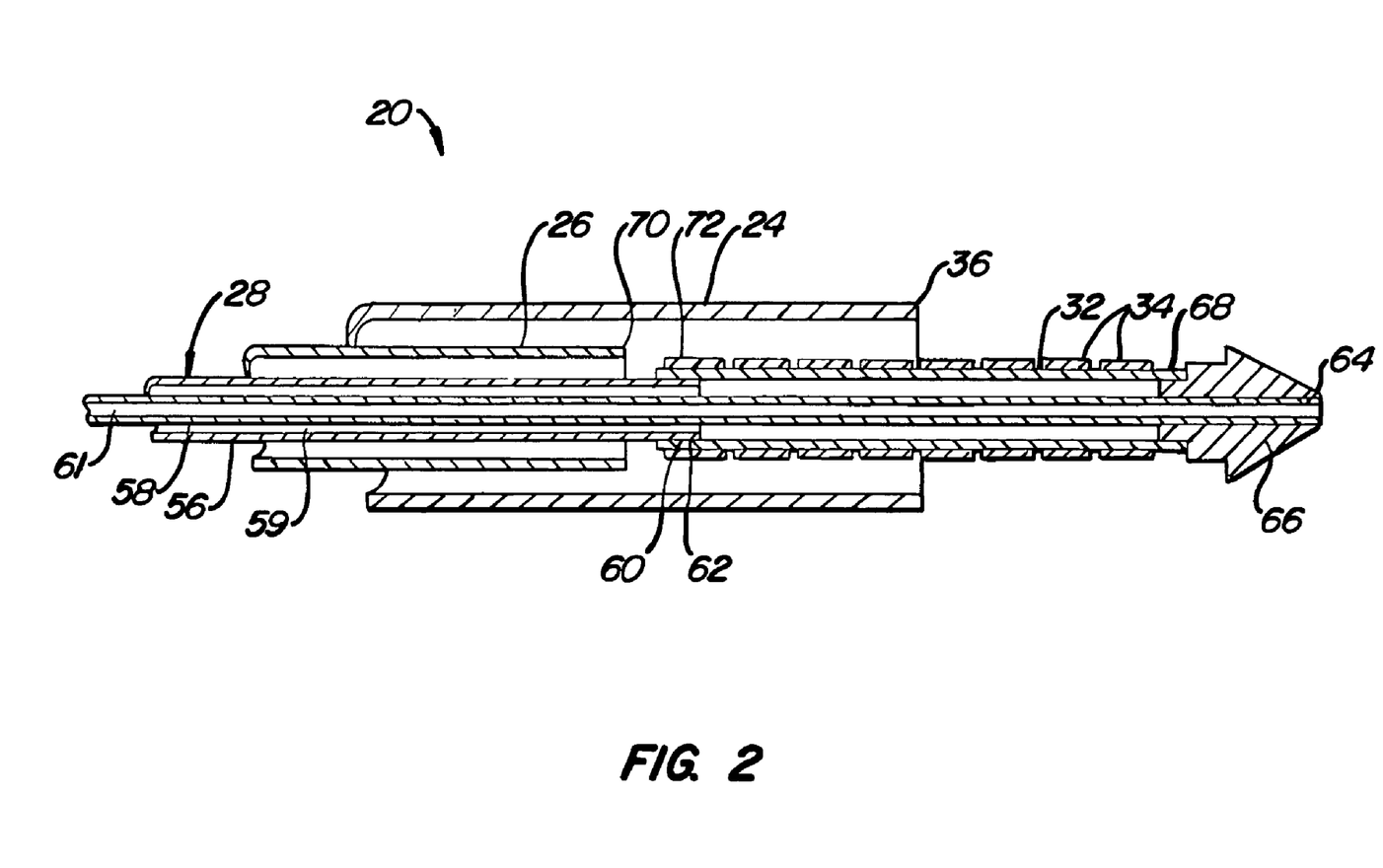
FIG. 2 is a side cross-sectional view of a distal portion of the stent deployment system of FIG. 1.

FIG. 2 shows a cross-section of a distal portion of stent deployment system 20 with expandable member 32 in an unexpanded condition. It may be seen that catheter shaft 28 has a tubular outer shaft 56 and a tubular inner shaft 58, defining a coaxial inflation lumen 59 therebetween. Outer shaft 56 and inner shaft 58 are both fixed to adaptor 48 and thus fixed relative to each other. Inner shaft 58 defines a guidewire lumen 61. Outer shaft 56 has a distal end 60 to which is mounted a proximal end 62 of expandable member 32. Inner shaft 58 has a distal end 64 to which is mounted a tapered nosecone 66. A distal end 68 of expandable member 32 is bonded to nosecone 66. A plurality of stent segments 34 are disposed around expandable member 32 and, in a preferred embodiment, are slidable relative thereto. Pusher tube 26 has a distal end 70 configured to engage a proximal stent segment 72 to exert a distal force thereon. Sheath 24 is disposed around pusher tube 26, a proximal portion of expandable member 32, and stent segments 34 thereon. It may be appreciated that an inflation fluid such as saline introduced into inflation lumen 59 will fill the interior of expandable member 32 causing it to expand, thus expanding stent segments 34.

Figure 3:
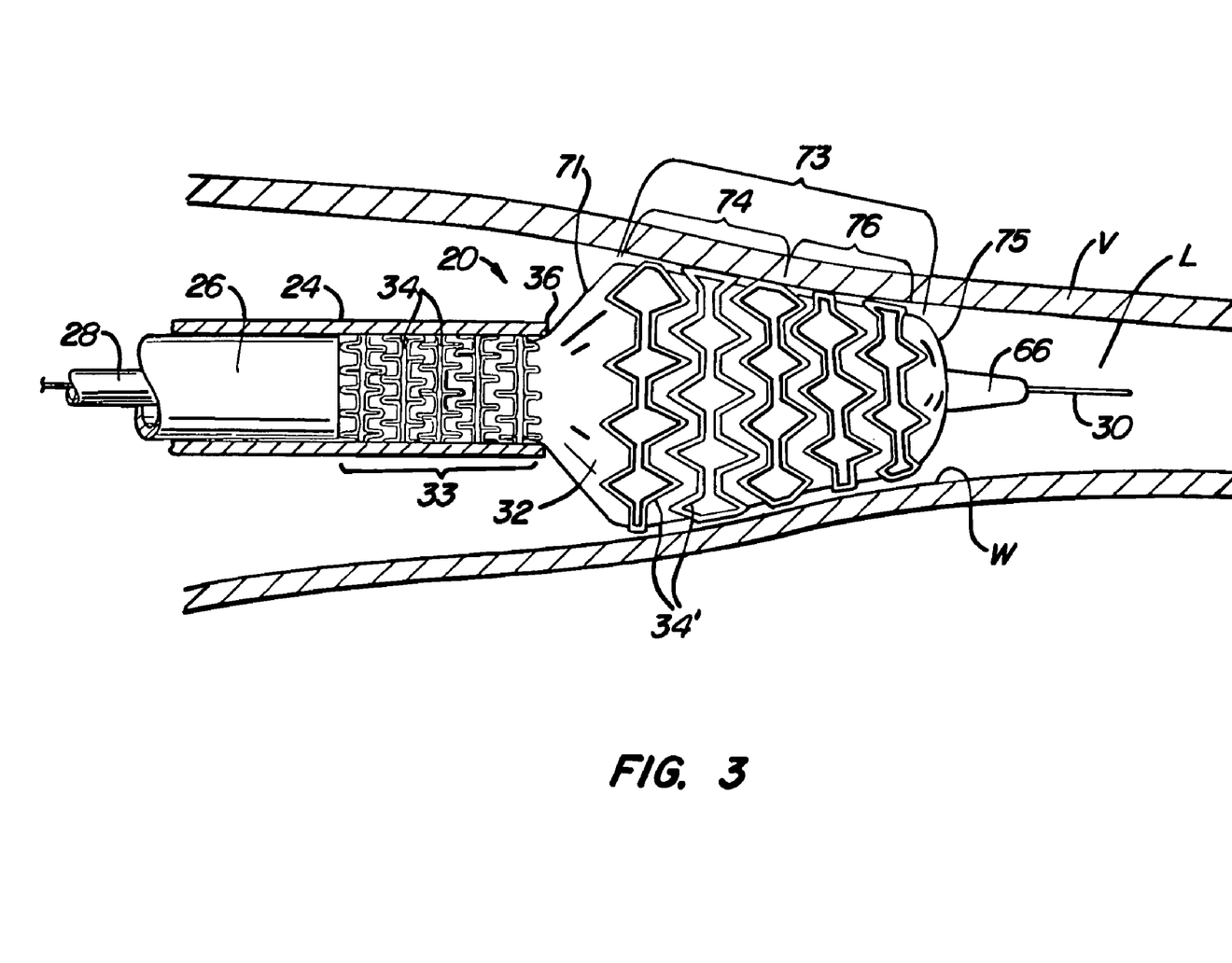
FIG. 3 is a partial side cross-sectional view of a distal portion of the stent deployment system of FIG. 1 positioned in a vessel.

FIG. 3 illustrates stent deployment system 20 in use in a vessel V. Initially sheath 24 is positioned over expandable member 32 (and stent segments 34 thereon) and the user positions stent deployment system 20 within the vascular region to be treated. Sheath 24 is then retracted proximally relative to expandable member 32 in order to expose the desired length of the expandable member 32 to be expanded and the desired number of stent segments 34' to be deployed. Inflation fluid is then introduced through inflation lumen 59 into expandable member 32, causing it to expand stent segments 34' into engagement with vessel wall W. Sheath 24 constrains expansion of a proximal portion 33 of expandable member 32 while that portion of expandable member 32 exposed distally of sheath 24 is allowed to expand along with the stent segments 34' thereon.

In its expanded condition, expandable member has a proximal end portion 71 having a reverse taper, a working portion 73 on which stent segments 34 are disposed, and a distal end portion 75 tapering down from working portion 73 to nosecone 66. In a preferred embodiment, working portion 73 has a tapered exterior shape in the expanded condition so as to have a larger expanded diameter in a proximal extremity 74 than its expanded diameter in a distal extremity 76. The expanded diameters are selected to provide optimal expansion within the tapered lumen L in vessel V so that all of the deployed stent segments 34' firmly engage vessel wall W. In a preferred embodiment suitable for coronary applications, expandable member 32 tapers from an expanded diameter of about 3–5 mm in proximal extremity 74 to an expanded diameter of about 2–4 mm in distal extremity 76. Expandable member 32 will preferably have a continuous taper of constant slope throughout all of proximal extremity 74 and distal extremity 76, usually having a slope of about 0.5–5%. Alternatively, proximal extremity 74 may taper at a different slope than distal extremity 76, or, as described below, either proximal extremity 74 or distal extremity 76 may have no taper or be only partially tapered along its length.

Following deployment of stent segments 34', expandable member 32 is deflated and retracted proximally within sheath 24. As expandable member 32 is retracted, distal force is maintained upon pusher tube 26 to hold stent segments 34 in position as expandable member 32 slides proximally through stent segments 34. The outer surface of expandable member 32 is configured to allow it to slide proximally through stent segments 34, being sufficiently smooth and lubricious and lacking notches or other surface features that would inhibit the proximal sliding movement of expandable member 32 through stent segments 34. It will be understood, however, that expandable member 32 may have some types of surface features and geometries that do not excessively inhibit such sliding movement, examples of which are described below. Expandable member 32 is positioned so that the distal-most stent segment 34 is disposed around the distal end of working portion 73. Stent deployment system 20 may then be repositioned to another vascular region to be treated, whereupon sheath 24 may be retracted to expose a desired number of stent segments 34, and the process repeated.

Figure 4:
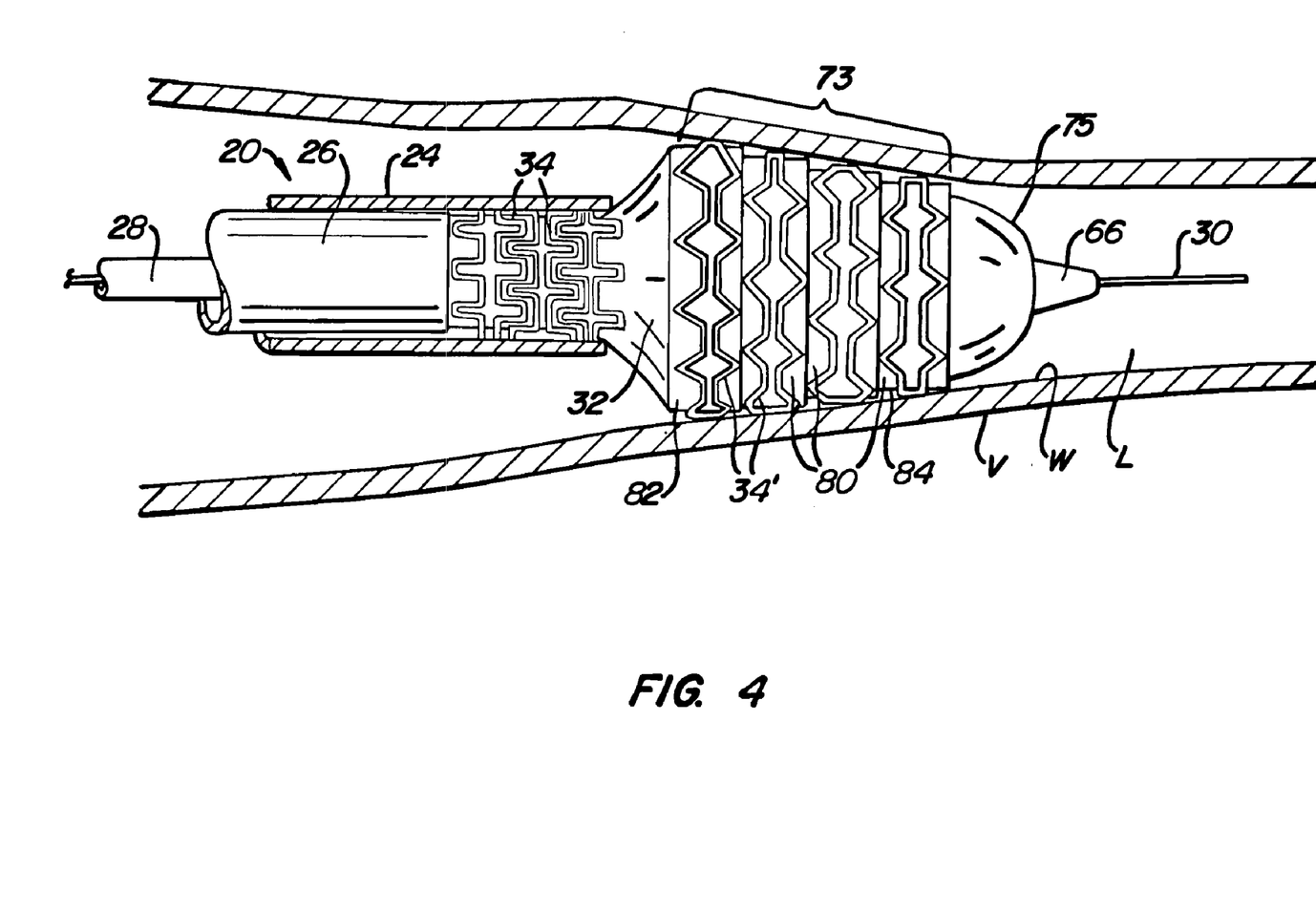
FIG. 4 is a partial side cross-sectional view of a distal portion of a further embodiment of a stent deployment system according to the invention.

FIG. 4 illustrates a further embodiment of stent deployment system 20 in which expandable member 32 has a plurality of cylindrical steps 80 of decreasing diameter in the distal direction. In a preferred embodiment, steps 80 are provided along the entire length of working portion 73, each step 80 being configured to accommodate a preselected number of stent segments 34. It may be seen that by sliding sheath 24 relative to expandable member 32, the desired number of steps 80 may be exposed for expansion of stent segments 34'. In one embodiment, each step 80 has an axial length approximately equal to the axial length of one stent segment 34 so that each step 80 holds one stent segment 34. For coronary applications, the axial length of one stent segment is preferably in the range of 2–5 mm. Each step has an expanded diameter slightly smaller than that of the adjacent step on its proximal side. In one embodiment, the proximal step 82 has an expanded diameter in a range of 3–5 mm, and the distal step 84 has an expanded diameter in a range of 2–4 mm. Each step between proximal step 82 and distal step 84 has an incrementally smaller diameter calculated by taking the difference between the diameters of the proximal step 82 and distal step 84 and dividing by the number of steps between the two. It should be understood that each step 80 may be of constant expanded diameter along its axial length, or some or all of steps 80 may be tapered so that the proximal end of step 80 has a larger expanded diameter than a distal end of step 80.

Figure 5:
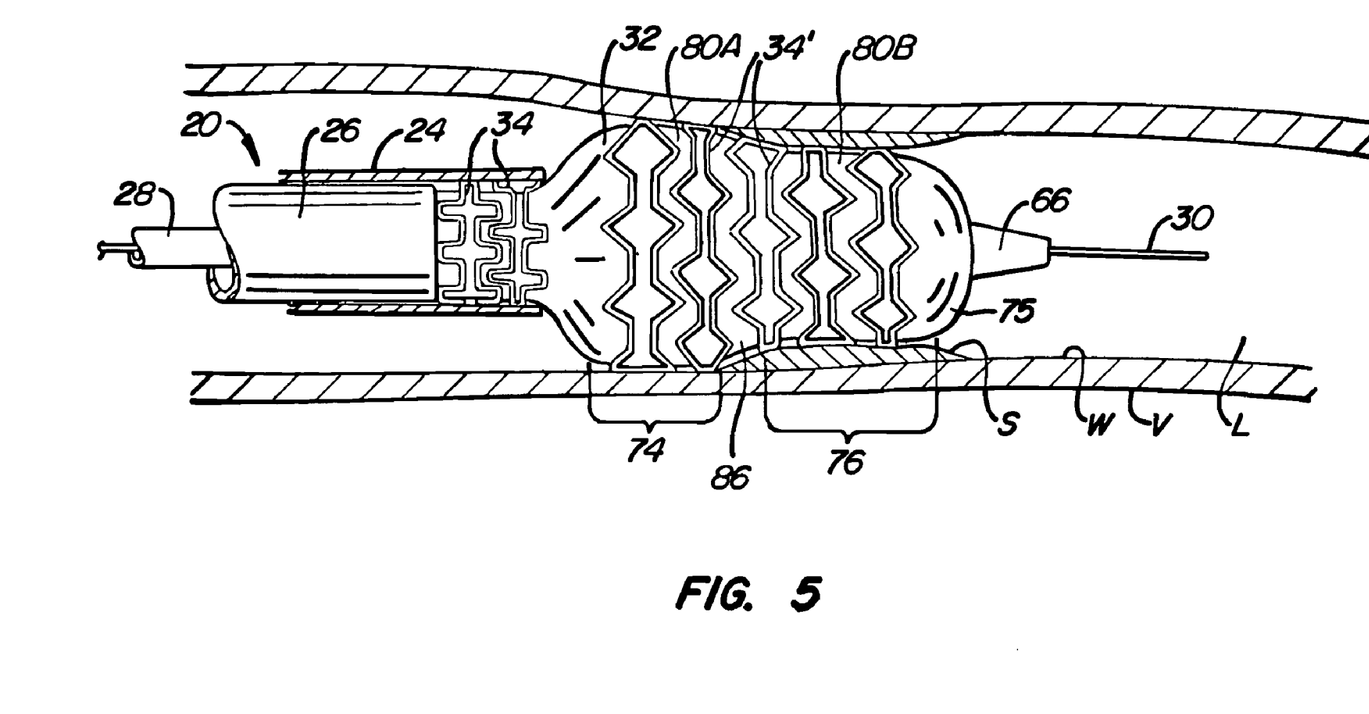
FIG. 5 is a partial side cross-sectional view of a distal portion of a further embodiment of a stent deployment system according to the invention.

In an alternative embodiment, shown in FIG. 5, expandable member 32 has only two steps 80A, 80B, one being of larger diameter in proximal extremity 74, and one being of smaller diameter in distal extremity 76. While steps 80A, 80B may be adjacent to one another with a radial wall in between as in FIG. 4, in the embodiment of FIG. 5 steps 80A, 80B are separated by a tapered portion 86. Each of steps 80A, 80B may be non-tapered with constant expanded diameter, or either step may taper in the distal direction. In one embodiment, proximal step 80A has an expanded diameter of about 3–5 mm and an axial length of about 5–15 mm, and distal step 80B has an expanded diameter of about 2–4 mm and an axial length of about 5–15 mm. Sheath 32 may be slidably positioned over expandable member 32 to expose the desired number of stent segments 34', thereby adjusting the exposed length of proximal step 80A and potentially distal step 80B.

In an exemplary method, stent deployment system 20 of FIG. 5 is positioned such that distal step 80B is within a stenotic lesion S in vessel V and proximal step 80A is adjacent to the proximal end of lesion S. In this way, expandable member 32 expands to a larger diameter proximal to lesion S where vessel V has a larger diameter, thereby ensuring that stent segments 24' are fully expanded into engagement with vessel wall W.

Figure 6A:
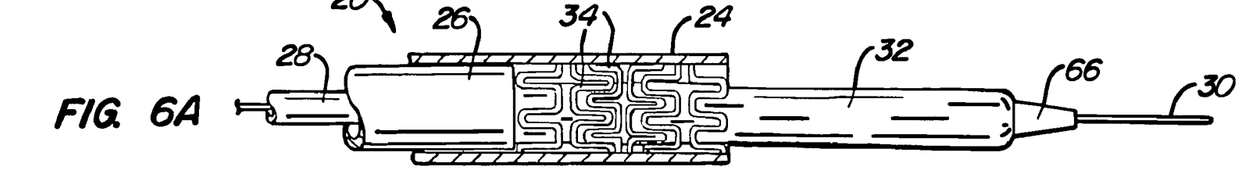
FIGS. 6A–6D are partial side cross-sectional views of a distal portion of the stent deployment system of FIG. 1 showing various steps in a method of use thereof.
Figure 6B:
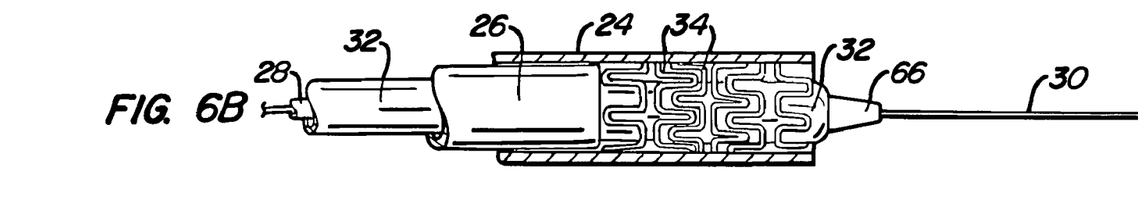

FIGS. 6A–6D illustrate the use of stent deployment system 20. FIG. 6A shows stent deployment system 20 within a vessel after deploying one or more stent segments 34. Expandable member 32 is disposed distally of sheath 24 and has no stent segments 34 on the exposed portion of expandable member 32. In order to treat another region of the vessel, expandable member 32 is retracted within sheath 24 while distal force is maintained upon pusher tube 26 to hold stent segments 34 in position as expandable member 32 moves proximally through the stent segments. Of course, it will be understood that expandable member 32 may alternatively be held in position while sliding pusher tube 26 and sheath 24 distally to slide stent segments 34 over expandable member 32. Stent segments 34 are positioned so that the distal-most stent segment is near the distal end of expandable member 32, as shown in FIG. 6B. To facilitate this alignment, nosecone 66 may have an enlarged proximal end portion (not shown) configured to engage and stop stents segments 34 from further movement.

Figure 6C:
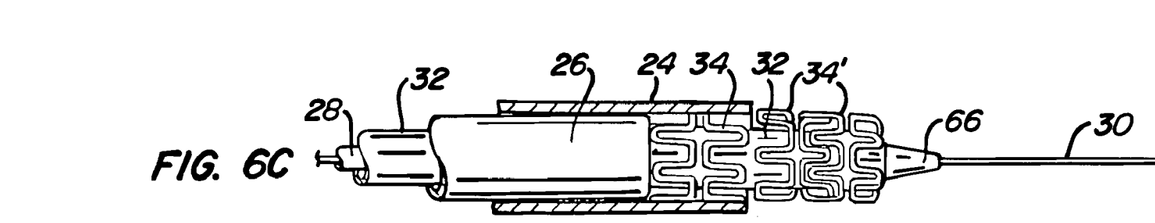

Stent deployment system 20 may then be repositioned to a different region in the vessel to be treated. Once repositioned, sheath 24 is retracted proximally relative to expandable member 32 while maintaining pressure on pusher tube 26 to expose the desired number of stent segments 34' to be deployed. Preferably, sheath 24 is then retracted an additional small distance without exerting force on pusher tube 26 so that stent segments 34 within sheath 24 are separated slightly from those stent segments 34' to be deployed, as shown in FIG. 6C. This ensures that stent segments 34 within sheath 24 are not expanded or dislodged when expandable member 32 is expanded. To facilitate this, a stent valve (not shown) may be provided at the distal end of sheath 24 to selectively engage stent segments 34 and retain them within the sheath, as described in commonly-assigned copending application Ser. No. 10/412,714, filed Apr. 10, 2003, which is incorporated herein by reference.

Figure 6D:
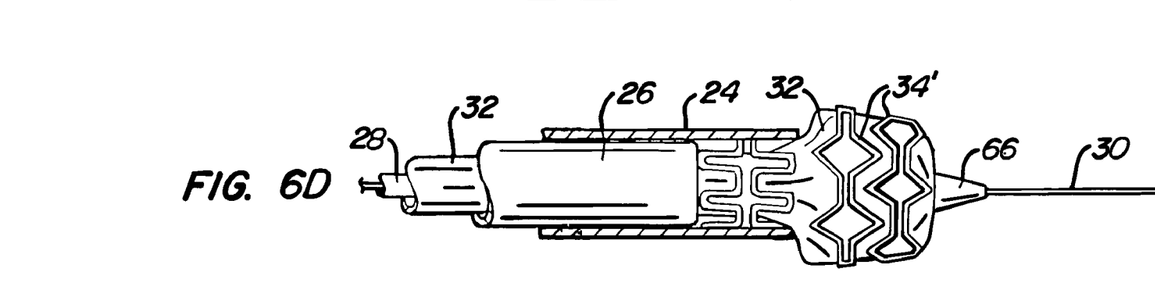

With the desired number of stent segments 34' exposed distally of sheath 24, expandable member 32 is expanded by introducing an inflation fluid through inflation lumen 59. This exerts a radial force on stent segments 34' causing them to expand and plastically deform into an expanded shape in engagement with the vessel wall, as shown in FIG. 6D. Expandable member 32 may then be deflated and retracted into sheath 24. This process may be repeated to treat multiple lesions of various lengths within a vessel or series of vessels without removing the stent deployment system from the patient's body.

As noted above, in preferred embodiments, expandable member 32 of stent deployment system 20 is configured to allow slidable movement of stent segments 34 distally relative to the expandable member. However, expandable member 32 should also prevent stent segments 34 from sliding proximally once they are positioned on expandable member 32. This becomes particularly challenging when sheath 24 is being retracted proximally relative to expandable member 32 and stent segments 34. Sheath 24 may engage stent segments 34 and urge them in the proximal direction relative to expandable member 32. In order to help maintain the position of stent segments 34 on expandable member 32, expandable member 32 may have surface features that engage stent segments 34 and preferentially allow them to slide distally over the expandable member while inhibiting them from sliding proximally over the expandable member. In one embodiment, illustrated in FIGS. 7A–7C, expandable member 32 has a plurality of resilient and flexible projections 88 that project outwardly and in the distal direction from the surface of expandable member 32. Projections 88 are angled toward the distal end of expandable member 32 so as to create a "grain" on the surface of expandable member 32 whereby stent segments 34 slide easily in the distal direction, but are inhibited from sliding in the proximal direction due to engagement with the distal tips 90 of projections 88. Projections 88 are preferably an elastomeric material and are formed integrally with the expandable member 32 by molding or dipping, but alternatively may be attached to the surface of expandable member 32 by adhesive, heat welding, or other means. As a further alternative, a fabric or sheet having suitable "grained" characteristics may be fixed to the surface of expandable member 32.

Preferably, projections 88 are arranged on expandable member 32 so as to project within spaces between or within stent segments 34. In one embodiment, shown schematically in FIG. 7B, projections 88 are arranged in a series of annular rows on expandable member 32, the rows being spaced apart a distance selected to fall within the spaces between each stent segment 34.

Figure 7A:
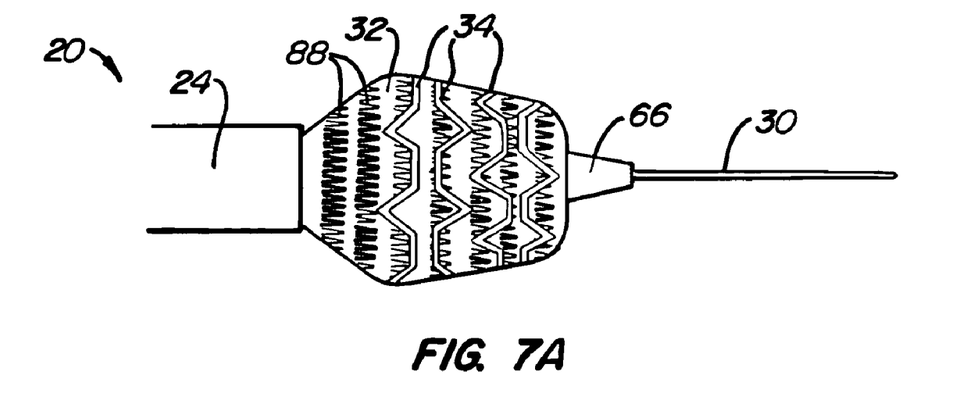
FIG. 7A is a side view of a distal portion of a further embodiment of a stent deployment system according to the invention.
Figure 7B:
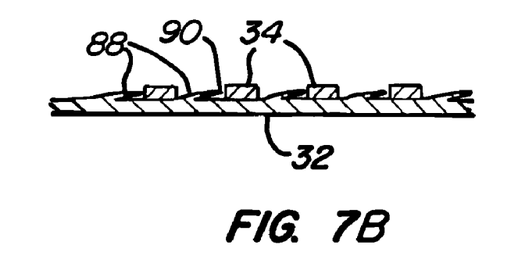
FIG. 7B is a side cross-sectional view of an expandable member of the stent deployment system of FIG. 7A.
Figure 7C:
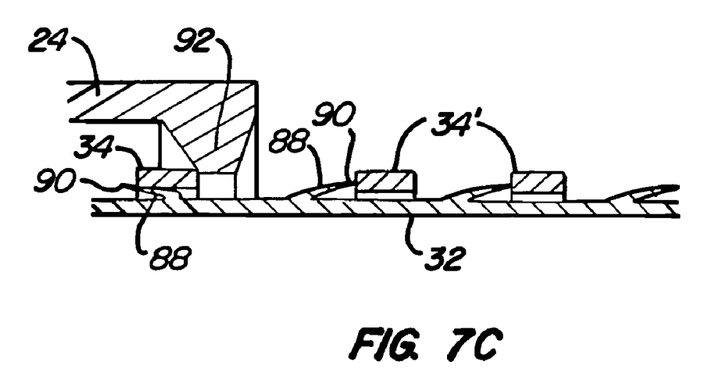
FIG. 7C is a side cross-sectional close-up view of a distal portion of the stent deployment system of FIG. 7A.

In some circumstances it may be desirable to move stent segments 34 proximally relative to expandable member 32. For example, as described above, when the desired number of stent segments 34 have been exposed distally of sheath 24 for deployment, it is often desirable to move the stent segments 34' within sheath 24 a short distance proximally relative to expandable member 32. As shown in FIG. 7C, in response to sufficient force in the proximal direction, projections 88 are configured to bend in the proximal direction to allow stent segments to move proximally relative to expandable member 32. In the embodiment shown, a stent valve 92 is disposed at the distal end of sheath 24, as described in copending application Ser. No. 10/412,714, filed Apr. 10, 2003, which has been incorporated herein by reference. Stent valve 92 is configured to engage stent segments 34 and exert sufficient proximal force against them to bend projections 88 to with distal tips 90 pointing proximally, allowing stent segments 34 to move proximally relative to expandable member 32. When it is desired to deploy stent segments 34 distally of sheath 24, force can be exerted on pusher tube 26 to urge stent segments 34 past stent valve 92.

Projections 88 may also be formed so as to project more or less outwardly in response to tension or relaxation in the wall of expandable member 32. For example, when expandable member 32 is deflated and not under tension, projections 88 can be configured to be normally lying flat against the outer surface of expandable member 32. When the wall of expandable member 32 is tensioned or stretched slightly, either by applying a distal force to inner shaft 58 relative to outer shaft 56 (FIG. 2), or by partially inflating expandable member 32, projections 88 will project further outwardly to increase engagement with stent segments 34. Alternatively, projections 88 may be configured to normally extend further outwardly when expandable member 32 is deflated and not under tension, inhibiting proximal movement of stent segments 34 over expandable member 32. When expandable member 32 is inflated or tensioned, projections 88 can be configured to lie flat against the outer surface of expandable member 32 to decrease interference with stent segments 34. In this manner, the user may control the degree of engagement between projections 88 and stent segments 34. For example, when retracting expandable member 32 proximally relative to stent segments 34, very little resistance to sliding movement over the expandable member is desirable. When sheath 24 is being retracted to expose the desired number of stent segments, however, a high degree of resistance to proximal movement of stent segments 32 is needed. Then, when the desired number of stent segments 34 has been exposed distally of sheath 24, it may be desirable to pull the remaining stent segments within sheath 24 further in the proximal direction relative to expandable member 32. At this point, it is desirable to minimize interference with the movement of stent segments 34 within sheath 24. By applying and releasing tension or by partially inflating and deflating expandable member 32, the user can selectively inhibit or allow movement of stent segments 34 relative to expandable member 32 in each of these situations.

Figure 8A:
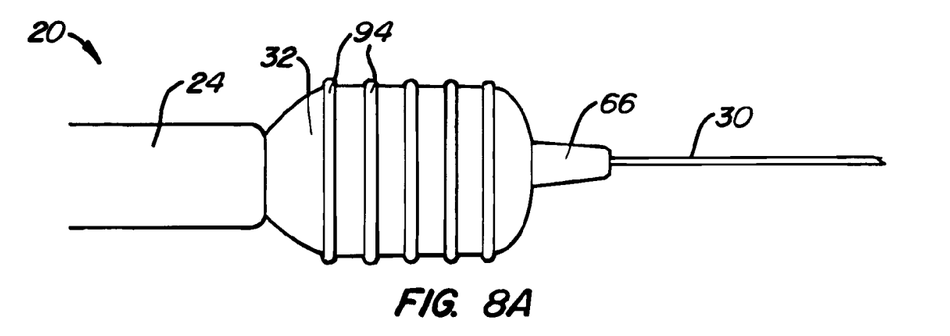
FIG. 8A is a side view of a distal portion of a further embodiment of a stent deployment system according to the invention.
Figure 8B:
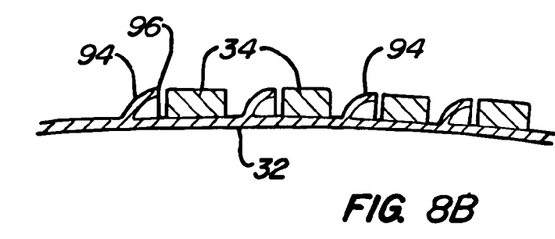
FIG. 8B is a side cross-sectional view of an expandable member of the stent deployment system of FIG. 8A.
Figure 8C:
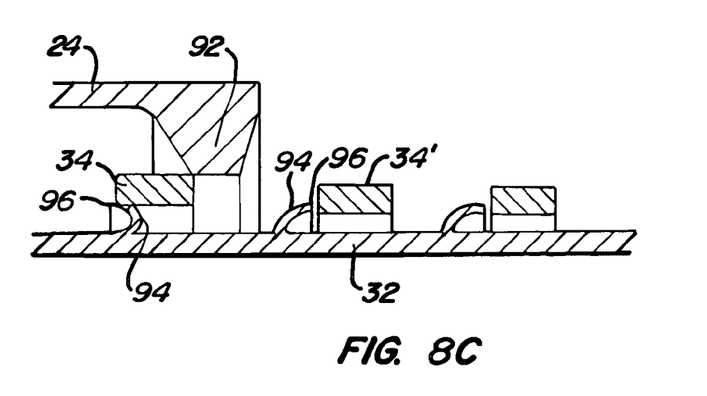
FIG. 8C is a side cross-sectional close-up view of a distal portion of the stent deployment system of FIG. 8A.

A further embodiment of expandable member 32 in stent deployment system 20 is illustrated in FIGS. 8A–8C. In this embodiment, expandable member 32 has a plurality of flexible, resilient annular ribs 94 configured to engage stent segments 34 (not shown for clarity). In cross section, as shown in FIG. 8B, each ribs 94 has a wall that curves in the distal direction so as to be convex on the proximal side and concave on the distal side with an outer edge 96 oriented in the distal direction. This allows stent segments 34 to slide relatively easily over ribs 94 distally, but inhibits proximal movement of stent segments 34 over ribs 94. Ribs 94 may be integrally formed with expandable member 32 or may be formed separately and fixed thereto by adhesive, heat welding or other means. Preferably, ribs 94 are spaced apart a distance corresponding to the axial length of stent segments 34 so that stent segments 34 are disposed between ribs 34.

It may be seen in FIG. 8C that ribs 94 are preferably deflectable or evertable in the proximal direction in response to sufficient force against stent segments 34. In the embodiment shown, stent valve 92 engages stent segment 34 and exerts a proximal force thereon as sheath 24 is retracted relative to expandable member 32. The outer edge 96 of rib 94 is deflected in the proximal direction, everting rib 94 and allowing stent segment 34 to move proximally over it. It should further be appreciated that ribs 94 may be configured to extend further outwardly or lie more flat against the surface of expandable member 32 in response to applying tension to or inflating expandable member 32 in a manner similar to that described above in connection with FIGS. 7A–7C. This permits the user to selectively control the degree of engagement with stent segments 34.

Figure 9:
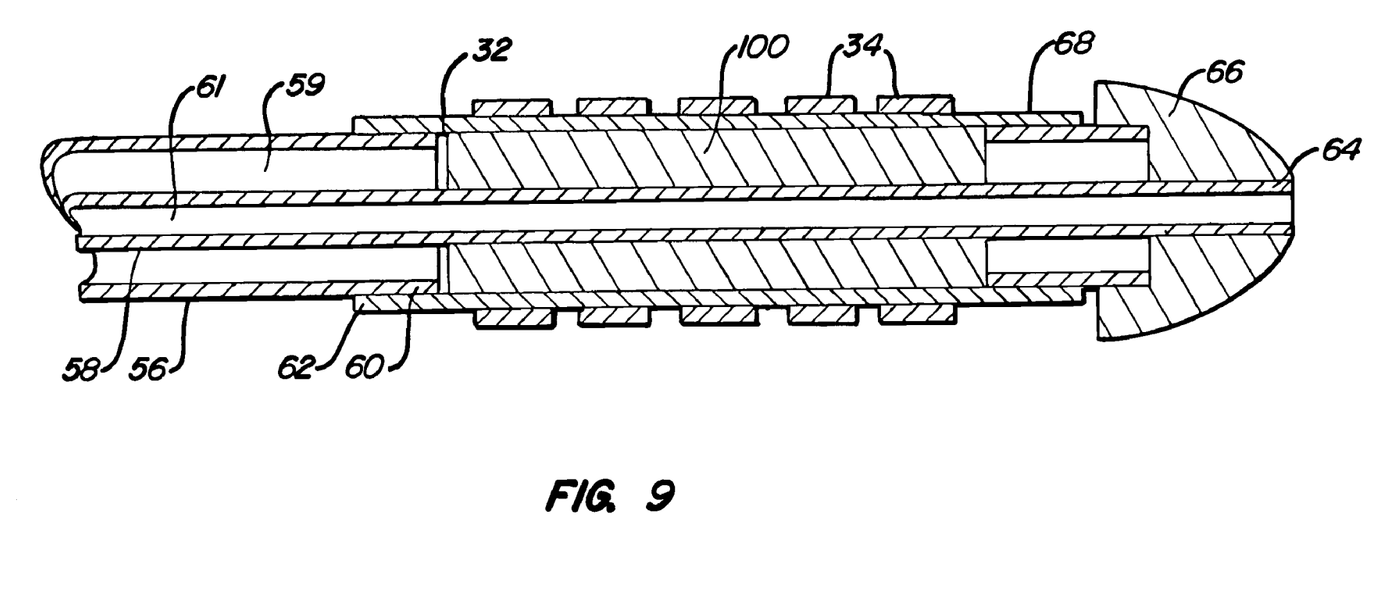
FIG. 9 is a side cross-sectional view of a distal portion of a further embodiment of a stent deployment system according to the invention.

A further embodiment of a stent deployment system according to the invention is shown in FIG. 9, in which sheath 24 and pusher tube 26 are removed for purposes of clarity. In this embodiment, a core member 100 is mounted to a distal portion of inner shaft 58 within the interior of expandable member 32. Expandable member 32 extends around core member 100 and is unattached thereto so that it may expand outwardly from core member 100 when inflation fluid is introduced via inflation lumen 59. Stent segments 34 are disposed on expandable member 34 and are crimped to press inwardly against core member 100 while still remaining axially slidable on expandable member 32. Core member 100 has a transverse dimension (outer diameter) typically about the same or just smaller than the deflated diameter of expandable member 32 so as to allow stent segments 34 to be crimped into engagement therewith but not crimped so much as to prevent stent segments 34 from sliding on expandable member 32. Core member 100 is composed of a compressible, resilient elastomer that presses outwardly against stent segments 34 to create friction between expandable member 32 and stent segments 34, creating resistance to slidable motion of the stent segments. In this way, stent segments 34 tend to remain stationary on expandable member 32 unless sufficient force is exerted on the stent segments by pusher tube 26 or sheath 24. This gives the user greater control in positioning a selected number stent segments 34 on expandable member 32 and retracting other stent segments 34 relative to expandable member 32 so as to deploy the desired number of stent segments.

While the above is a complete description of the preferred embodiments of the invention, various additions, alternatives, modifications, equivalents and substitutions are possible without departing from the scope thereof. Therefore, the above should not be taken to limit the scope of the invention, which is defined by the appended claims.

What is claimed is:

1. A stent deployment system for deploying one or more stents in a blood vessel having a luminal taper, the stent deployment system comprising:
    an elongated catheter shaft having a proximal end and a distal end;
    an expandable member mounted to the catheter shaft near the distal end, the expandable member having an outer surface and a proximal extremity and a distal extremity, the proximal extremity having a first expanded diameter and the distal extremity having a second expanded diameter, the first expanded diameter being larger than the second expanded diameter in general correspondence to the luminal taper; and
    a plurality of separately deployable stent segments slidably positionable on the proximal and distal extremities for expansion therewith;
    wherein at least a first and a second of the stent segments can be expanded simultaneously by the expandable member, the first stent segment being positioned on the proximal extremity and expanded to a larger diameter than the second stent segment positioned on the distal extremity.

2. The stent deployment system of claim 1 wherein at least one of the first and second extremities of the expandable member has an axial length selected to accommodate a pre-selected number of stent segments.

3. The stent deployment system of claim 1 wherein the pre-selected number of stent segments is one.

4. The stent deployment system of claim 1 wherein at least one of the first and second extremities has a constant outer diameter.

5. The stent deployment system of claim 1 wherein at least one of the first and second extremities has a tapered outer diameter.

6. The stent deployment system of claim 5 wherein both of the first and second extremities are tapered.

7. The stent deployment system of claim 4 wherein another of the first and second extremities has a constant outer diameter.

8. The stent deployment system of claim 1 wherein the proximal and distal extremities are contiguous.

9. The stent deployment system of claim 8 wherein the outer surface is continuously tapered along the proximal and distal extremities.

10. The stent deployment system of claim 1 wherein the expandable member has a proximal end portion fixed to the catheter shaft at a first location and a distal end portion fixed to the catheter shaft at a second location, the proximal end portion having a reverse taper between the first location and the proximal extremity, the distal end portion having a distal taper between the distal extremity and the second location, the expandable member being tapered between the proximal end portion and the distal end portion at a slope substantially less than the slope of the distal taper.

11. The stent deployment system of claim 9 wherein the outer surface is tapered at a slope of about 0.5 to 5%.

12. The stent deployment system of claim 1 wherein the first diameter is about 3–5 mm and the second diameter is about 2–4 mm.

13. The stent deployment system of claim 1 further comprising a pusher for slidably advancing the stent segments distally relative to the expandable member.

14. The stent deployment system of claim 13 wherein the pusher comprises a tubular member slidably disposed over the catheter shaft and having a distal end for engaging a stent segment.

15. The stent deployment system of claim 1 wherein the expandable member is adapted to expand a first plurality of stent segments simultaneously while a second plurality of stent segments remains unexpanded.

16. The stent deployment system of claim 15 further comprising a sheath slidably disposed over at least a proximal portion of the expandable member, the second plurality of stent segments being disposed on the proximal portion, the sheath being configured to restrain expansion of the proximal portion and the second plurality of stents.

17. The stent deployment system of claim 1 wherein the outer surface comprises a series of steps of decreasing outer diameter as the distal end is approached.

18. The stent deployment system of claim 17 wherein each step has an axial length selected to accommodate a pre-selected number of stent segments.

19. The stent deployment system of claim 18 wherein the pre-selected number is one.

20. A stent deployment system for deploying one or more stents in a blood vessel having a luminal taper, the stent deployment system comprising:
    an elongated catheter shaft having a proximal end and a distal end;

an expandable member mounted to the catheter shaft near the distal end, the expandable member being tapered when expanded from a first expanded diameter in a proximal extremity thereof to a second expanded diameter in a distal extremity thereof in general correspondence to the luminal taper; and a plurality of separately deployable stent segments slidably positionable over the expandable member to locations on the proximal and distal extremities for expansion therewith;

wherein at least a first and a second of the stent segments can be expanded simultaneously by the expandable member, the first stent segment being positioned on the proximal extremity and expanded to a larger diameter than the second stent segment positioned on the distal extremity.

21. The stent deployment system of claim 20 wherein the expandable member is tapered continuously from the first expanded diameter to the second expanded diameter.

22. The stent deployment system of claim 20 wherein the expandable member has a proximal end portion fixed to the catheter shaft at a first location and a distal end portion fixed to the catheter shaft at a second location, the proximal end portion having a reverse taper between the first location and the proximal extremity, the distal end portion having a distal taper between the distal extremity and the second location, the expandable member being tapered between the proximal end portion and the distal end portion at a slope substantially less than the slope of the distal taper.

23. The stent deployment system of claim 20 wherein the expandable member is tapered at a slope of about 0.5–5%.

24. The stent deployment system of claim 20 wherein the first diameter is about 3–5 mm and the second diameter is about 2–4 mm.

25. The stent deployment system of claim 20 further comprising a pusher for slidably advancing the stent segments distally relative to the expandable member.

26. The stent deployment system of claim 25 wherein the pusher comprises a tubular member slidably disposed over the catheter shaft and having a distal end for engaging a stent segment.

27. The stent deployment system of claim 20 wherein the expandable member is adapted to expand a first plurality of stent segments simultaneously while a second plurality of stent segments remains unexpanded.

28. The stent deployment system of claim 27 further comprising a sheath slidably disposed over at least a proximal portion of the expandable member, the second plurality of stent segments being disposed on the proximal portion, the sheath being configured to restrain expansion of the proximal portion and the second plurality of stents.

* * * * *